United States Patent
Broderick et al.

(10) Patent No.: US 10,450,264 B2
(45) Date of Patent: Oct. 22, 2019

(54) SYNTHESIS OF NON-CYCLIC AMIDE AND THIOAMIDE BASED IONIC LIQUIDS

(71) Applicant: UOP LLC, Des Plaines, IL (US)

(72) Inventors: Erin M. Broderick, Arlington Heights, IL (US); Avram M. Buchbinder, Chigago, IL (US); Alakananda Bhattacharyya, Glen Ellyn, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 15/866,393

(22) Filed: Jan. 9, 2018

(65) Prior Publication Data

US 2018/0127352 A1 May 10, 2018

Related U.S. Application Data

(63) Continuation of application No. PCT/US2016/041031, filed on Jul. 6, 2016.

(60) Provisional application No. 62/190,952, filed on Jul. 10, 2015.

(51) Int. Cl.
C07C 233/89 (2006.01)
C07C 231/12 (2006.01)
C07C 2/58 (2006.01)

(52) U.S. Cl.
CPC ............. *C07C 233/89* (2013.01); *C07C 2/58* (2013.01); *C07C 231/12* (2013.01); C07C 2527/125 (2013.01)

(58) Field of Classification Search
None
See application file for complete search history.

(56) References Cited

U.S. PATENT DOCUMENTS

| | | |
|---|---|---|
| 3,155,642 A | 11/1964 | Duck et al. |
| 3,170,904 A | 2/1965 | Ueda et al. |
| 3,170,906 A | 2/1965 | Ueda et al. |
| 3,457,321 A | 7/1969 | Hambling et al. |
| 3,483,268 A | 12/1969 | Hambling et al. |
| 3,483,269 A | 12/1969 | Hambling et al. |
| 3,505,425 A | 4/1970 | Jones et al. |
| 3,562,351 A | 2/1971 | Mertzweiller et al. |
| 3,592,869 A | 7/1971 | Cannell |
| 3,644,564 A | 2/1972 | van Zwet et al. |
| 3,663,451 A | 5/1972 | Hill |
| 3,679,772 A | 7/1972 | Yoo |
| 3,697,617 A | 10/1972 | Yoo et al. |
| 3,755,490 A | 8/1973 | Yoo et al. |
| 3,914,430 A | 10/1975 | Hughes |
| 3,954,668 A | 5/1976 | Yoo et al. |
| 3,981,941 A | 9/1976 | Butter |
| 4,520,221 A | 5/1985 | Hsia Chen |
| 4,547,613 A | 10/1985 | Garwood et al. |
| 4,642,404 A | 2/1987 | Shihabi |
| 4,659,343 A | 4/1987 | Kelly |
| 4,757,042 A | 7/1988 | Threlkel |
| 4,764,440 A | 8/1988 | Jones et al. |
| 5,104,840 A | 4/1992 | Chauvin et al. |
| 5,284,989 A | 2/1994 | Apelian et al. |
| 5,824,832 A | 10/1998 | Sherif et al. |
| 5,895,830 A | 4/1999 | Stine et al. |
| 6,686,511 B2 | 2/2004 | Miller et al. |
| 7,053,261 B2 | 5/2006 | Herbst et al. |
| 7,544,813 B2 | 6/2009 | Harmer et al. |
| 8,070,939 B2 | 12/2011 | Hommeltoft et al. |
| 8,613,865 B2 | 12/2013 | Choi et al. |
| 9,096,480 B2 | 8/2015 | Smith et al. |
| 9,096,481 B2 | 8/2015 | Smith et al. |
| 9,096,482 B2 | 8/2015 | Smith et al. |
| 9,096,485 B2 | 8/2015 | Smith et al. |
| 9,102,577 B2 | 8/2015 | Smith et al. |
| 9,102,578 B2 | 8/2015 | Smith et al. |
| 9,126,881 B2 | 9/2015 | Smith et al. |
| 2004/0059173 A1 | 3/2004 | Houzvicka et al. |
| 2008/0021254 A1 | 1/2008 | Schmidt et al. |
| 2010/0224063 A1* | 9/2010 | Choi ................. B01D 53/1475 95/236 |
| 2011/0229401 A1* | 9/2011 | Dai ........................ C01B 32/05 423/445 R |
| 2013/0001092 A1 | 1/2013 | Abbott et al. |
| 2013/0012699 A1 | 1/2013 | Choi et al. |

(Continued)

FOREIGN PATENT DOCUMENTS

| CN | 1798731 A | 7/2006 |
|---|---|---|
| CN | 1944439 A | 4/2007 |

(Continued)

OTHER PUBLICATIONS

Bonner, "The Raman spectra of the hydrochloride salts of N-methylacetamide", Spectrochimica Acta, 1966, vol. 22, pp. 1125-1129.

(Continued)

*Primary Examiner* — Clinton A Brooks
*Assistant Examiner* — Kofi Adzamli

(57) ABSTRACT

Non-cyclic amide or thioamide based ionic liquids and methods of making them are disclosed. The non-cyclic amide or thioamide based ionic liquid comprises a cation and an anion and has the formula:

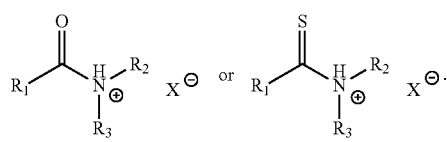

19 Claims, No Drawings

(56) References Cited

U.S. PATENT DOCUMENTS

| | | |
|---|---|---|
| 2013/0206672 A1 | 8/2013 | Harness et al. |
| 2014/0165829 A1 | 6/2014 | Sharma et al. |
| 2014/0171710 A1 | 6/2014 | Mahieux et al. |
| 2015/0005540 A1 | 1/2015 | Smith et al. |
| 2015/0059577 A1 | 3/2015 | Lokhandwala |
| 2018/0127334 A1 | 5/2018 | Broderick et al. |

FOREIGN PATENT DOCUMENTS

| | | |
|---|---|---|
| CN | 101234994 A | 8/2008 |
| CN | 101941986 A | 1/2011 |
| CN | 102146165 A | 8/2011 |
| CN | 103071367 A | 5/2013 |
| GB | 1123474 | 8/1968 |
| KR | 1071774 B1 | 10/2011 |
| WO | 2010074835 A2 | 7/2010 |

OTHER PUBLICATIONS

Cook, "Protonated Carbonyl Groups IV. N,N-Dimethylacetamide Salts", Canadian Journal of Chemistry, (1964) vol. 42, pp. 2721-2727.

Guo, "Oxa-Michael addition catalyzed by amide-based acidic ionic liquids", Chinese Journal of Catalysis, (2011), 32 (1), 162-165. Language: Chinese, Database: CAPLUS.

Kumler, "Structure of Salts of N,N-Dimethylacetamide and N,N-Di(n)butylacetamide", Salts of N,N-Dimethylacetamide, (Dec. 20, 1961), pp. 4983-4985.

Spinner, "The vibration spectra and structures of the hydrochlorides of urea, thiourea and acetamide. The basic properties of amides and thioamides", Spectrochimica Acta, 1959, pp. 95-109.

Zaleska, "Perhydropyrimidinylium and 1,3-diazepinylium salts as potential ionic liquids", ARKIVOC 2007 (vi) 64-74.

Zhang, "Characterizing the Structural Properties of N,N-Dimethylformamide-Based Ionic Liquid: Density-Functional Study", J. Phys. Chem. B 2007, 111, 11016-11020.

Search Report dated Oct. 20, 2016 for corresponding PCT Appl. No. PCT/US2016/041031.

Guo, "Oxa-Michael addition catalyzed by amide-based acidic ionic liquids", Cuihua Xuebao (2011), 32(1), 162-165, Language: Chinese.

Search Report dated Oct. 20, 2016 from PCT application No. PCT/US2016/040969.

Coleman, et al. "Liquid Coordination Complexes Formed by the Heterolytic Cleavage of Metal Halides", Angew. Chem. Int. Ed., 2013, 52, 12582-12586.

* cited by examiner

SYNTHESIS OF NON-CYCLIC AMIDE AND THIOAMIDE BASED IONIC LIQUIDS

CROSS-REFERENCE TO RELATED APPLICATIONS

This application is a Continuation of International Application No. PCT/US2016/041031 filed Jul. 6, 2016 which application claims benefit of U.S. Provisional Application No. 62/190,952 filed Jul. 10, 2015, now expired, the contents of which cited applications are hereby incorporated by reference in their entirety.

BACKGROUND OF THE INVENTION

Ionic liquids are of interest to industry because of their wide range of applications, including use as solvents and catalysts. Ionic liquids are salts comprised of cations and anions which typically melt below about 100° C.

Ionic liquids are described in U.S. Pat. Nos. 4,764,440, 5,104,840, and 5,824,832, for example. The properties vary extensively for different ionic liquids, and the use of ionic liquids depends on the properties of a given ionic liquid. Depending on the organic cation of the ionic liquid and the anion, the ionic liquid can have very different properties.

However, the cost of ionic liquids has limited the widespread adoption of ionic liquids.

There is a need for lower cost ionic liquids and for methods of making them.

SUMMARY OF THE INVENTION

One aspect of the invention is a non-cyclic amide or thioamide based ionic liquid. In one embodiment, the non-cyclic amide or thioamide based ionic liquid comprises a cation and an anion and has the formula:

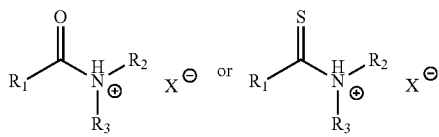

wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group, and $R_2$ and $R_3$ form a $C_4$-$C_{12}$ cycloalkyl group, a $4_1$-$C_{12}$ cycloalkenyl group, a substituted $C_4$-$C_{12}$ cycloalkyl group, or a substituted $C_4$-$C_{12}$ cycloalkenyl group; and $X^-$ is an anion.

Another aspect of the invention is a method of making a non-cyclic amide or thioamide based ionic liquid. In one embodiment, the method includes reacting a non-cyclic amide or thioamide having a general formula:

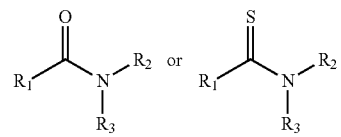

with a Brønsted acid HX to form an amidium or thioamidium halide reaction product. The amidium or thioamidium halide reaction product can optionally be reacted with a metal halide to form an amidium or thioamidium halometallate reaction product. $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a cycloalkyl $C_4$-$C_{12}$ group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group.

DETAILED DESCRIPTION OF THE INVENTION

The present invention provides non-cyclic amide or thioamide based ionic liquids. The non-cyclic amide or thioamide based ionic liquids can be produced by reacting a non-cyclic amide or thioamide with a strong acid. In some embodiments, the reaction product of the non-cyclic amide or thioamide and the strong acid is reacted with a metal halide. By non-cyclic amide or thioamide based ionic liquids, we mean ionic liquids in which the amide or thioamide bond in the cation is not contained in a cyclic structure. However, the cation can contain cyclic structures in other parts of the cation.

The non-cyclic amide or thioamide based ionic liquid comprises a cation and an anion and has the general formula:

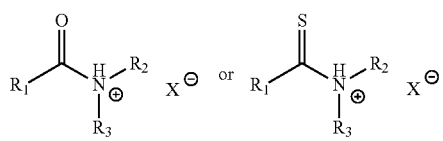

wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group; and $X^-$ is an anion.

By substituted, we mean that the alkyl group, alkenyl group, etc. includes a group including, but not limited to, a halide, such as chloride, bromide, iodide, or fluoride, a $C_2$-$C_{12}$ ether group, a silyl group, a hydroxyl group, a thiol group, a cyano group, a sulfonyl group, an amine group, a nitrile group, a thiocyanate group, or combinations thereof.

Another way to represent

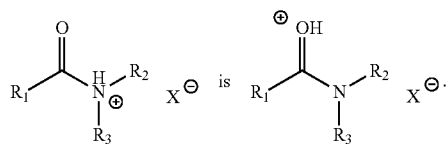

We intend both representations to be covered by the first structure.

Another way to represent

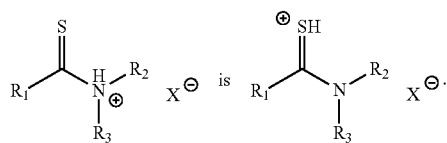

We intend both representations to be covered by the first structure.

Suitable anions include, but are not limited to carboxylates, nitrates, phosphates, phosphinates, phosphonates, imides, cyanates, borates, sulfates (including bisulfates), sulfonates (including fluoroalkanesulfonates), acetates, halides, halometallates, and combinations thereof. Examples of $X^-$ groups include, but are not limited to, tetrafluoroborate, triflate, trifluoroacetate, chloroacetate, nitrate, hydrogen sulfate, hydrogen phosphate, dicyanoimide, methylsulfonate, and combinations thereof.

In some embodiments, $X^-$ is a halide, such as chloride, bromide, iodide, or fluoride. In some embodiments, when $X^-$ is a halide, the mol ratio of cation to anion is about 1:1.

In other embodiments, $X^-$ is a halometallate. In some embodiments, the metal in the halometallate comprises Sn, Al, Zn, Mn, Fe, Ga, Cu, Ni, Co, In, or combinations thereof. In some embodiments, the halide in the halometallate comprises bromide, chloride, iodide, fluoride, or combinations thereof. One or more of the halides (but not all) can be substituted with an —OH group, for example, $Al_3Cl_9OH$. Suitable halometallates include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $InCl_4^-$, $InCl_5^{2-}$, $InCl_6^{3-}$, or combinations thereof. In some embodiments, when X is the halometallate, the mol fraction of metal in the halometallate is in the range of about 0.25 to about 1.

Suitable cations include, but are not limited to, N,N-dimethylacetamidium, acetamidium, carbonyl diamidium, thioamidium, N-methylthioacetamidium, N,N-dimethylthioacetamidium, N-methylacetamidium, N,N-dimethylformamidium, benzamidium, N-methylbenzamidium, N,N-dimethylbenzamidium, or dichloroacetamidium.

Suitable non-cyclic amide or thioamide based ionic liquids include, but are not limited to, N,N-dimethylacetamidium chloride, N,N-dimethylacetamidium bromide, N,N-dimethylacetamidium $AlCl_4$, N,N-dimethylacetamidium $Al_2Cl_7$, acetamidium chloride, acetamidium bromide, acetamidium $AlCl_4$, acetamidium $Al_2Cl_7$, urea chloride, urea bromide, urea $AlCl_4$, urea $Al_2Cl_7$, thioacetamidium chloride, thioacetamidium bromide, thioacetamidium $AlCl_4$, thioacetamidium $Al_2Cl_7$, N-methylthioacetamidium chloride, N-methylthioacetamidium bromide, N-methylthioacetamidium $AlCl_4$, N-methylthioacetamidium $Al_2Cl_7$, N,N-dimethylthioacetamidium chloride, N,N-dimethylthioacetamidium bromide, N,N-dimethylthioacetamidium $AlCl_4$, N,N-dimethylthioacetamidium $Al_2Cl_7$, N-methylacetamidium chloride, N-methylacetamidium bromide, N-methylacetamide $AlCl_4$, N-methylacetamidium $Al_2Cl_7$, N,N-dimethylformamidium chloride, N,N-dimethylformamidium bromide, N,N-dimethylformamidium $AlCl_4$, or N,N-dimethylformamidium $Al_2Cl_7$.

The non-cyclic amide or thioamide based ionic liquids can be made by reacting a non-cyclic amide or thioamide having a general formula:

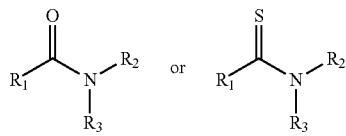

with a Brønsted acid HX to form an amidium or thioamidium reaction product;

wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group.

In some embodiments, the non-cyclic amide or thioamide comprises N,N-dimethylacetamide, acetamide, urea, thioacetamide, N-methylthioacetamide, N,N-dimethylthioacetamide, N-methylacetamide, N,N-dimethylformamide, benzamide, N-methylbenzamide, N,N-dimethylbenzamide, or dichloroacetamide.

In some embodiments, the Brønsted acid HX is at least one of hydrochloric acid, hydrobromic acid, hydroiodic acid, sulfuric acid, nitric acid, phosphoric acid, tetrafluoroboric acid, sulfonic acid, triflic acid, toluenesulfonic acid dihaloacetic acid, and trihaloacetic acid.

The mol ratio of the non-cyclic amide or thioamide to the Brønsted acid HX is typically about 1:1.

The non-cyclic amide or thioamide is reacted with the Brønsted acid HX with or without a solvent. Suitable solvents include, but are not limited to, water, alcohols, such as methanol or ethanol, dichloromethane, chloroform, or toluene.

The reaction can be performed at room temperature and atmospheric pressure. Higher or lower temperatures and/or pressures could be used, if desired.

The reaction time to form the non-cyclic amidium or thioamidium reaction product is generally in the range of about 1 min to about 1 hr.

In some embodiments, the anion is a halide, and the non-cyclic amidium or thioamidium reaction product is a non-cyclic amidium or thioamidium halide reaction product. In some embodiments, the non-cyclic amidium or thioamidium halide reaction product is reacted with a metal halide to form an amidium or thioamidium halometallate reaction product.

In some embodiments, the mol ratio of the cation to the metal in the halometallate or of the amidium halide reaction product to the metal halide is typically in a range of about 1:0.8 to about 1:2.2, or about 1:1 to about 1:2.2, or in about 1:1.2 to about 1:2.2, or about 1:1.4 to about 1:2.2, or about 1:1.16 to about 1:2.2. The ratio may be affected by the specific cation used and the synthesis temperature.

In some embodiments, the metal of the metal halide comprises Sn, Al, Zn, Mn, Fe, Ga, Cu, Ni, Co, In, or combinations thereof. Suitable metal halides include, but are not limited to, $AlCl_3$, $AlCl_2Br$, $AlBr_3$, $GaCl_3$, $GaCl_2Br$, $CuCl_3$, $FeCl_3$, or $InCl_3$. In some embodiments, one or more (but not all) of the halide can be substituted with an —OH group.

The amidium or thioamidium halide reaction product can be reacted with the metal halide in the presence of a solvent. Suitable solvents include, but are not limited to, dichloromethane, chloroform, toluene, or benzene. Protic solvents are not desirable for this reaction because they could react with the metal halide.

The ratio of the metal to the halide in the halometallate is less than the ratio of metal atoms to halide atoms in the neutral metal halide. That is, the metal:halide ratio is less than 1:X, where X is the valence of the metal. For example, the ratio of metal to halide in $Al_2Cl_7$ is 2:7, whereas the ratio of $AlCl_3$ is 1:3.

The halide in the Brønsted acid HX can be the same as the halide in the metal halide, or it can be different.

The reaction of the amidium or thioamidium halide reaction product and the metal halide can be performed at room temperature and atmospheric pressure. Higher or lower temperatures and/or pressures could be used, if desired.

The reaction time to form the non-cyclic amidium or thioamidium halometallate is generally in the range of about 1 min to about 24 hr. The reaction time is affected by whether a solvent is used in the reaction with solvents increasing the rate of reaction.

The reaction of the amidium or thioamidium halide reaction product and the metal halide typically takes place under an inert atmosphere, such as nitrogen, argon, and the like.

The reactions (non-cyclic amide or thioamide with the Brønsted acid HX and/or amidium or thioamidium halide reaction product with the metal halide) may be practiced in laboratory scale experiments through full scale commercial operations. The process may be operated in batch, continuous, or semi-continuous mode.

EXAMPLES

Synthesis of N,N-Dimethylacetamidium Chloride

An HCl in ethanol solution (1.25M, 35 mL, 43.8 mmol) was added to N,N-dimethylacetamide (3.55 g, 40.2 mmol) at room temperature. After stirring for 1 h, the volatiles were removed at 50° C. under reduced pressure to yield a white solid. Yield: 4.87 g, 98%. $^1$H NMR (500 MHz, $CDCl_3$): 2.51 (s, 3H), 3.14 (s, 6H), 15.58 (s, 1H). $^{13}$C NMR (125 MHz, $CDCl_3$): 18.19, 38.67, 174.83.

Synthesis of N,N-Dimethylacetamidium Chloroaluminate

Under a nitrogen atmosphere, aluminum trichloride was slowly added to N,N-dimethylacetamidium chloride. Upon addition of the aluminum chloride with stirring, the mixture began to liquefy. The mixture was stirred 1.67 h with stirring until the material was completely liquefied. Yield: 11.2 g, 90.3%. $^1$H NMR (500 MHz, $CDCl_3$): 2.55 (s, 3H), 3.34 (d, 6H). $^{13}$C NMR (125 MHz, $CDCl_3$): 21.27, 39.39, 40.77, 173.02.

Alkylation Experiment

In a nitrogen atmosphere, N,N-dimethylacetamidium chloroaluminate was loaded into a 300 ml autoclave containing a baffle. Prior to loading, the autoclave and baffle had been dried for several hours above 100° C. The number of acid sites in the ionic liquid was adjusted to optimize the performance by addition of 2-chlorobutane. (The number of acid sites could be adjusted by changing the catalyst loading or by changing the amount of acid or acid precursor added.) The autoclave was charged with 80 g isobutane and pressurized with 3.4 MPa(g) (500 psig) of nitrogen. The contents were stirred at 1600 rpm, and 8 g 2-butene was added over time (about 118.72 mL/h) at room temperature. After 8 min, the reaction mixture was allowed to settle and the liquid product was sampled directly from the autoclave. The sample was passed through a silica column then analyzed by gas chromatography. The results are shown Table 1.

The groupings below include all isomers having the same carbon number. The % butenes conversion was calculated using 100−(the weight of butenes in the product divided by the weight of butenes added). RONC is the Research Octane Number Calculated. TMP/DMH is the weight ratio of trimethylpentanes to dimethylhexanes in the product. The % Selectivity is (wt % of that paraffin)/(sum of wt % of the $C_5$ and larger products formed). The yield is (the mass of $C_5$ and larger products formed)/(the mass of the $C_4$ olefin added).

TABLE 1

| | 3.8 g N,N-dimethylacetamidium chloroaluminate + 0.466 g 2-chlorobutane |
|---|---|
| Mol ratio cation:mol Al:chlorobutane | 1:1.8:0.4 |
| Vol % IL | 1.9 |
| Reaction Time | 8 min |
| i/o (mol ratio) | 7.9 |
| Butenes Conversion (%) | 95.2 |
| RONC | 95.0 |
| % Sel C8 | 73.7 |
| % Sel C9 | 11.6 |
| % Sel C5-7 | 14.7 |
| TMP/DMH | 13.9 |
| Yield (C5+/C4=) | 2.19 |

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

Specific Embodiments

While the following is described in conjunction with specific embodiments, it will be understood that this description is intended to illustrate and not limit the scope of the preceding description and the appended claims.

A first embodiment of the invention is a non-cyclic amide or thioamide based ionic liquid comprising a cation and an anion, the ionic liquid having a formula

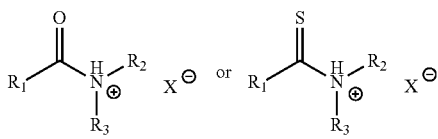

wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group; and $X^-$ is an anion. An embodiment of the invention is one, any or all of prior embodiments in this paragraph up through the first embodiment in this paragraph wherein the anion is a carboxylate, a nitrate, a phosphate, a phosphinate, a phosphonate, an imide, a cyanate, a borate, a sulfate, a sulfonate, an acetate, a halide, a halometallate, and combinations thereof. An embodiment of the invention is one, any or all of prior embodiments in this paragraph up through the first embodiment in this paragraph wherein the anion is the halide and wherein the halide is bromide, chloride, iodide, fluoride, or combinations thereof. An embodiment of the invention is one, any or all of prior embodiments in this paragraph up through the first embodiment in this paragraph wherein the anion is the halometallate, wherein the metal in the halometallate comprises Sn, Al, Zn, Mn, Fe, Ga, Cu, Ni, Co, In, or combinations thereof, and wherein the halide in the halometallate comprises bromide, chloride, iodide, fluoride, or combinations thereof, and wherein the halometallate optionally includes an —OH group. An embodiment of the invention is one, any or all of prior embodiments in this paragraph up through the first embodiment in this paragraph wherein the anion is the halometallate, and wherein the halometallate comprises $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $InCl_4^-$, $InCl_5^{2-}$, $InCl_6^{3-}$, or combinations thereof. An embodiment of the invention is one, any or all of prior embodiments in this paragraph up through the first embodiment in this paragraph wherein the cation comprises N,N-dimethylacetamidium, acetamidium, carbonyl diamidium, thioamidium, N-methylthioacetamidium, N,N-dimethylthioacetamidium, N-methylacetamidium, N,N-dimethylformamidium, benzamidium, N-methylbenzamidium, N,N-dimethylbenzamidium, or dichloroacetamidium. An embodiment of the invention is one, any or all of prior embodiments in this paragraph up through the first embodiment in this paragraph wherein the ionic liquid is N,N-dimethylacetamidium chloride, N,N-dimethylacetamidium bromide, N,N-dimethylacetamidium $AlCl_4$, N,N-dimethylacetamidium $Al_2Cl_7$, acetamidium chloride, acetamidium bromide, acetamidium $AlCl_4$, acetamidium $Al_2Cl_7$, urea chloride, urea bromide, urea $AlCl_4$, urea $Al_2Cl_7$, thioacetamidium chloride, thioacetamidium bromide, thioacetamidium $AlCl_4$, thioacetamidium $Al_2Cl_7$, N-methylthioacetamidium chloride, N-methylthioacetamidium bromide, N-methylthioacetamidium $AlCl_4$, N-methylthioacetamidium $Al_2Cl_7$, N,N-dimethylthioacetamidium chloride, N,N-dimethylthioacetamidium bromide, N,N-dimethylthioacetamidium $AlCl_4$, N,N-dimethylthioacetamidium $Al_2Cl_7$, N-methylacetamidium chloride, N-methylacetamidium bromide, N-methylacetamide $AlCl_4$, N-methylacetamidium $Al_2Cl_7$, N,N-dimethylformamidium chloride, N,N-dimethylformamidium bromide, N,N-dimethylformamidium $AlCl_4$, or N,N-dimethylformamidium $Al_2Cl_7$. An embodiment of the invention is one, any or all of prior embodiments in this paragraph up through the first embodiment in this paragraph wherein the anion is a halometallate and wherein a mol ratio cation to the metal in the halometallate is in a range of about 10.8 to about 12.2. An embodiment of the invention is one, any or all of prior embodiments in this paragraph up through the first embodiment in this paragraph wherein the anion is the halometallate and wherein a ratio of metal to halide in the halometallate is less than a ratio of the metal to the halide in a neutral metal halide. An embodiment of the invention is one, any or all of prior embodiments in this paragraph up through the first embodiment in this paragraph wherein the substituted $C_1$-$C_{12}$ alkyl group, the substituted $C_1$-$C_{12}$ alkenyl group, the substituted $C_4$-$C_{12}$ cycloalkyl group, the substituted $C_4$-$C_{12}$ cycloalkenyl group, or the substituted aryl group is substituted with a halide, a $C_2$-$C_{12}$ ether group, a silyl group, a hydroxyl group, a thiol group, a cyano group, a sulfonyl group, an amine group, a nitrile group, a thiocyanate group, or combinations thereof.

A second embodiment of the invention is a method of making a non-cyclic amide or thioamide based ionic liquid comprising reacting a non-cyclic amide or thioamide having a general formula

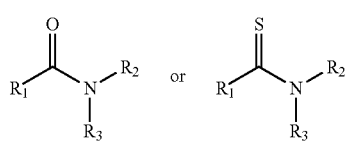

with a Brønsted acid HX to form an amidium or thioamidium reaction product wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_1$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group. An embodiment of the invention is one, any or all of prior embodiments in this paragraph up through the second embodiment in this paragraph wherein the Brønsted acid HX is at least one of hydrochloric acid, hydrobromic acid, hydroiodic acid, sulfuric acid, nitric acid, phosphoric acid, tetrafluoroboric acid, sulfonic acid, triflic acid, toluenesulfonic acid dihaloacetic acid, and trihaloacetic acid. An embodiment of the invention is one, any or all of prior embodiments in this paragraph up through the second embodiment in this paragraph wherein the Brønsted acid HX is at least one of the hydrochloric acid, the hydrobromic acid, and the hydroiodic acid, and further comprising reacting the amidium or thioamidium reaction product with a metal halide to form an amidium or thioamidium halometallate reaction product. An embodiment of the invention is one, any or all of prior embodiments in this paragraph up through the second embodiment in this paragraph wherein a metal of the metal halide comprises Sn, Al, Zn, Mn, Fe, Ga, Cu, Ni, Co, In, or combinations thereof. An embodiment of the invention is one, any or all of prior embodiments in this paragraph up through the second embodiment in this paragraph a mol ratio of the amidium or thioamidium reaction product to the metal halide is in a range of about 10.8 to about 12.2. An embodiment of the invention is one, any or all of prior embodiments in this paragraph up through the second embodiment in this paragraph wherein the amidium or thioamidium reaction product is reacted with the metal halide in the presence of a solvent selected from dichloromethane, chloroform toluene, or benzene. An embodiment of the invention is one, any or all of prior embodiments in this paragraph up through the second embodiment in this paragraph wherein the halide in the Brønsted acid HX is the same as the halide in the metal halide. An embodiment of the invention is one, any or all of prior embodiments in this paragraph up through the second embodiment in this paragraph wherein the non-cyclic amide or thioamide comprises N,N-dimethylacetamide, acetamide, urea, thioacetamide, N-methylthioacetamide, N,N-dimethylthioacetamide, N-methylacetamide, N,N-dimethylformamide, benzamide, N-methylbenzamide, N,N-dimethylbenzamide, or dichloroacetamide. An embodiment of the invention is one, any or all of prior embodiments in this paragraph up through the second embodiment in this paragraph wherein a mol ratio of the non-cyclic amide or thioamide to the Brønsted acid HX is about 11. An embodiment of the invention is one, any or all of prior embodiments in this paragraph up through the second embodiment in this paragraph wherein the non-cyclic amide or thioamide is reacted with the Brønsted acid HX in the presence of a solvent.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed:

1. A non-cyclic amide or thioamide based ionic liquid comprising a cation and an anion, the ionic liquid having a formula:

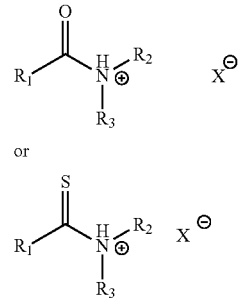

or wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group, wherein the substituted $C_1$-$C_{12}$ alkyl group, the substituted $C_1$-$C_{12}$ alkenyl group, the substituted $C_4$-$C_{12}$ cycloalkyl group, the substituted $C_4$-$C_{12}$ cycloalkenyl group, or the substituted aryl group is not substituted with a cyano group or a thiocyanate group; and $X^-$ is a nitrate, a phosphate, a phosphinate, a phosphonate, an imide, a borate, a sulfate, a sulfonate, an acetate, a halide, a halometallate, and combinations thereof.

2. The ionic liquid of claim 1 wherein the anion is the halide and wherein the halide is bromide, chloride, iodide, fluoride, or combinations thereof.

3. The ionic liquid of claim 1 wherein the anion is the halometallate, wherein the metal in the halometallate comprises Sn, Al, Zn, Mn, Fe, Ga, Cu, Ni, Co, In, or combinations thereof, and wherein the halide in the halometallate comprises bromide, chloride, iodide, fluoride, or combinations thereof, and wherein the halometallate optionally includes an —OH group.

4. The ionic liquid of claim 1 wherein the anion is the halometallate, and wherein the halometallate comprises $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $InCl_4^-$, $InCl_5^{2-}$, $InCl_6^{3-}$, or combinations thereof.

5. The ionic liquid of claim 1 wherein the cation comprises N,N-dimethylacetamidium, acetamidium, carbonyl diamidium, thioamidium, N-methylthioacetamidium, N,N-dimethylthioacetamidium, N-methylacetamidium, N,N-dimethylformamidium, benzamidium, N-methylbenzamidium, N,N-dimethylbenzamidium, or dichloroacetamidium.

6. The ionic liquid of claim 1 wherein the ionic liquid is N,N-dimethylacetamidium chloride, N,N-dimethylacetamidium bromide, N,N-dimethylacetamidium $AlCl_4$, N,N-dimethylacetamidium $Al_2Cl_7$, acetamidium chloride, acetamidium bromide, acetamidium $AlCl_4$, acetamidium $Al_2C_7$, urea chloride, urea bromide, urea $AlCl_4$, urea $Al_2Cl_7$, thioacetamidium chloride, thioacetamidium bromide, thioacetamidium $AlCl_4$, thioacetamidium $Al_2Cl_7$, N-methylthioacetamidium chloride, N-methylthioacetamidium bromide, N-methylthioacetamidium $AlCl_4$, N-methylthioacetamidium $Al_2Cl_7$, N,N-dimethylthioacetamidium chloride, N,N-dimethylthioacetamidium bromide, N,N-dimethylthioacetamidium $AlCl_4$, N,N-dimethylthioacetamidium $Al_2Cl_7$, N-methylacetamidium chloride, N-methylacetamidium bromide, N-methylacetamide $AlCl_4$, N-methylacetamidium $Al_2Cl_7$, N,N-dimethylformamidium chloride, N,N-dimethylformamidium bromide, N,N-dimethylformamidium $AlCl_4$, or N,N-dimethylformamidium $Al_2Cl_7$.

7. The ionic liquid of claim 1 wherein the anion is a halometallate and wherein a mol ratio cation to the metal in the halometallate is in a range of about 1:0.8 to about 1:2.2.

8. The ionic liquid of claim 1 wherein the anion is the halometallate and wherein a ratio of metal to halide in the halometallate is less than a ratio of the metal to the halide in a neutral metal halide.

9. The ionic liquid of claim 1 wherein the substituted $C_1$-$C_{12}$ alkyl group, the substituted $C_1$-$C_{12}$ alkenyl group, the substituted $C_4$-$C_{12}$ cycloalkyl group, the substituted $C_4$-$C_{12}$ cycloalkenyl group, or the substituted aryl group is substituted with a halide, a $C_2$-$C_{12}$ ether group, a silyl group, a hydroxyl group, a thiol group, a sulfonyl group, an amine group, a nitrile group, or combinations thereof.

10. A method of making a non-cyclic amide or thioamide based ionic liquid comprising:
reacting a non-cyclic amide or thioamide having a general formula:

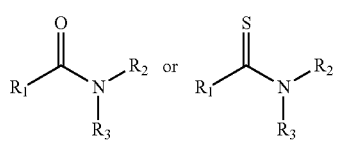

with a Brønsted acid HX to form an amidium or thioamidium reaction product wherein $R_1$, $R_2$, and $R_3$ are independently selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_2$-$C_{12}$ ether group, or a silyl group; or wherein $R_1$ is selected from hydrogen, halide, a $C_1$-$C_{12}$ alkyl group, a $C_1$-$C_{12}$ alkenyl group, a $C_4$-$C_{12}$ cycloalkyl group, a $C_4$-$C_{12}$ cycloalkenyl group, an aryl group, a substituted $C_1$-$C_{12}$ alkyl group, a substituted $C_1$-$C_{12}$ alkenyl group, a substituted $C_4$-$C_{12}$ cycloalkyl group, a substituted $C_4$-$C_{12}$ cycloalkenyl group, a substituted aryl group, a $C_1$-$C_{12}$ ether group, or a silyl group, and $R_2$ and $R_3$ form a $C_4$-$C_{12}$ cycloalkyl group, a $C_4$-$C_{12}$ cycloalkenyl group, a substituted $C_4$-$C_{12}$ cycloalkyl group, or a substituted $C_4$-$C_{12}$ cycloalkenyl group, wherein the substituted $C_1$-$C_{12}$ alkyl group, the substituted $C_1$-$C_{12}$ alkenyl group, the substituted $C_4$-$C_{12}$ cycloalkyl group, the substituted $C_4$-$C_{12}$ cycloalkenyl group, or the substituted aryl group is not substituted with a cyano group or a thiocyanate group; and wherein an anion in the Brønsted acid HX is a nitrate, a phosphate, a phosphinate, a phosphonate, an imide, a borate, a sulfate, a sulfonate, an acetate, a halide, a halometallate, and combinations thereof.

11. The method of claim 10 wherein the Brønsted acid HX is at least one of hydrochloric acid, hydrobromic acid, hydroiodic acid, sulfuric acid, nitric acid, phosphoric acid, tetrafluoroboric acid, sulfonic acid, triflic acid, toluenesulfonic acid dihaloacetic acid, and trihaloacetic acid.

12. The method of claim 10 wherein the Brønsted acid HX is at least one of the hydrochloric acid, the hydrobromic acid, and the hydroiodic acid, and further comprising reacting the amidium or thioamidium reaction product with a metal halide to form an amidium or thioamidium halometallate reaction product.

13. The method of claim 12 wherein a metal of the metal halide comprises Sn, Al, Zn, Mn, Fe, Ga, Cu, Ni, Co, In, or combinations thereof.

14. The method of claim 12 a mol ratio of the amidium or thioamidium reaction product to the metal halide is in a range of about 1:0.8 to about 1:2.2.

15. The method of claim 12 wherein the amidium or thioamidium reaction product is reacted with the metal halide in the presence of a solvent selected from dichloromethane, chloroform toluene, or benzene.

16. The method of claim 12 wherein the halide in the Brønsted acid HX is the same as the halide in the metal halide.

17. The method of claim 10 wherein the non-cyclic amide or thioamide comprises N,N-dimethylacetamide, acetamide, urea, thioacetamide, N-methylthioacetamide, N,N-dimethylthioacetamide, N-methylacetamide, N,N-dimethylformamide, benzamide, N-methylbenzamide, N,N-dimethylbenzamide, or dichloroacetamide.

18. The method of claim 10 wherein a mol ratio of the non-cyclic amide or thioamide to the Brønsted acid HX is about 1:1.

19. The method of claim 10 wherein the non-cyclic amide or thioamide is reacted with the Brønsted acid HX in the presence of a solvent.

* * * * *